(12) United States Patent
Handa et al.

(10) Patent No.: US 7,118,766 B2
(45) Date of Patent: Oct. 10, 2006

(54) PHARMACEUTICAL COMPOSITION AND PROCESS FOR ISOLATION OF TRANS-TETRACOS-15-ENOIC ACID AND METHOD OF TREATMENT FOR HEPATOTOXICITY

(75) Inventors: Sukhdev Swami Handa, Jammu (IN); Bupinder Singh, Jammu (IN); Bal Krishan Chandan, Jammu (IN); Ajit Kumar Saxena, Jammu (IN); Vikram Bhardwaj, Jammu (IN); V. N. Gupta, Jammu (IN); Om Parkash Suri, Jammu (IN); Naresh Kumar Satti, Jammu (IN); Krishan Avtar Suri, Jammu (IN)

(73) Assignee: Council of Scientific & Industrial Research, New Dehli (IN)

( * ) Notice: Subject to any disclaimer, the term of this patent is extended or adjusted under 35 U.S.C. 154(b) by 0 days.

(21) Appl. No.: 10/073,548

(22) Filed: Feb. 11, 2002

(65) Prior Publication Data

US 2003/0175363 A1 Sep. 18, 2003

(51) Int. Cl.
*A01N 65/00* (2006.01)
(52) U.S. Cl. .................................. 424/725
(58) Field of Classification Search ............ 424/725
See application file for complete search history.

(56) References Cited

U.S. PATENT DOCUMENTS 4,767,618 A * 8/1988 Grollier et al. .............. 424/74

5,897,865 A * 4/1999 Nguyen ....................... 424/756

FOREIGN PATENT DOCUMENTS

| JP | 49019039 | * | 2/1974 |
| JP | 401211519 | * | 8/1989 |
| WO | WO 99/11223 | * | 3/1999 |

OTHER PUBLICATIONS

Anand, K.K., et al., "Protective Effect of Alcoholic Extract of Indigofera tinctoria Linn. In Experimental Liver Injury", Indian Journal of Experimental Biology, vol. 17, pp. 685-687, (1979).
Anand, K.K., et. al., "Histological Evidence of Protection by Indigofera tinctoria Linn. Against Carbontetracholoride Induced Hepatotoxicity—An Experimental Study", Indian Journal of Experimental Biology, vol. 19, pp. 208-300, (1981).
Chopra, R.N., et al., Glossary of Indian Medicinal Plants, Council of Scientific & Industrial Research New Delhi, p. 141 (1956).
Curtius, H. Ch., et al., "Glycogen and Enzymes of Glycogen Metabolism", Clinical Biochemistry Principles and Methods, vol. II, pp. 1208-1235, (1974).
Lowry, Oliver H., et al., "Protein Measurement with the Folin Phenol Reagent", The Journal of Biological Chemistry, vol. 193, pp. 265-275 (1951).
Nadkarni, K.M., Indian Materia Medica, vol. 1, p. 680, (1954).
Szasz, Gabor, "Reaction-Rate Method for γ-Glutamyltransferase Activity in Serum", Clinical Chemistry, vol. 22, No. 12, pp. 2051-2055.

* cited by examiner

*Primary Examiner*—Michael Meller
(74) *Attorney, Agent, or Firm*—Fish & Richardson P.C.

(57) ABSTRACT

The present invention relates to a pharmaceutical composition comprising a bioactive constituent trans-tetracos-15-enoic acid and a process for the isolation of tetracos-15-enoic acid from the plant *Indigofera tinctoria* along with a method of treatment for hepatotoxicity.

11 Claims, No Drawings

PHARMACEUTICAL COMPOSITION AND PROCESS FOR ISOLATION OF TRANS-TETRACOS-15-ENOIC ACID AND METHOD OF TREATMENT FOR HEPATOTOXICITY

FIELD OF INVENTION

The present invention relates to a pharmaceutical composition comprising trans-tetracos-enoic acid and a process for the isolation of trans-tetracos-15-enoic acid from a plant source *Indigofera tinctoria*. The present invention also relates to a method of treatment for hepatotoxicity.

BACKGROUND AND PRIOR ART REFERENCES

*Indigofera tinctoria* Linn. (Family Leguminosae, Hindi-Neel) is an annual herbaceous shrub, 4–6 ft. high, found throughout India. Earlier it was cultivated in India, China and other eastern countries as a source of Indigo.

In an indigenous system of medicine, extract of this plant is used for the treatment of epilepsy, nervous disorders and bronchitis [Wealth of India, vol. 5 (Council of Scientific and Industrial Research, New Delhi) 182, (1959)]. The plant is also known to be used as an ointment for sores, old ulcers and haemorrhoids [R. N. Chopra, S. L. Nayar and I C Chopra, Glossary of Indian Medicinal Plants, 141 (1956)]. The leaves of the plant have been used in liver ailments [Nadkarni, K. M., Indian Materia Medica, vol. 1 (Popular Book Depot, Bombay, 680 (1954)].

Organic solvent extract of the leaves of the plant exhibited marked hepatoprotective effect against carbon tetrachloride induced hepatic injury in rabbits, rats and mice [Anand, K. K., Chand Dewan, Ghatak, B. J. Ray & Arya, R. K., Indian J. Expl. Biol. 19, 298 (1981), Anand, K. K., Chand Dewan & Ghatak, B. J. Ray, Indian J. Expl. Biol., 17, 685(1979)].

Literature survey revealed that earlier reports showed the presence of trans-tetracos-15-enoic acid in Jojoba oil ex. Simmondsia chinensis seeds (0.62–1.11%), c/s isomer of the acid in fatty acids of the seed oil of. Microula sikkimensis (1.2%). [Wang, Huiying, Yu, Xuefian, Yi, Yuanfen & Ding, Jingkai, Yunnan Zhiwu Yanjiu 1989 11 (I), 60-4 (Ch.), L, Jing Jingmin; Wang, Jingping; Yu, Feuglau. Zhiwn, Xuebao, 1989, 31 (1) 50-3; (Ch). These reports do not mention isolation of the constituent and the content estimation is based on GLC data.

The bioactive constituent thus isolated in the present invention from the plant *Indigofera tinctoria* is designated as RLJ-NE-598 (025)(F)(A$_3$) (TCA)

Hepatotoxins that cause acute hepatitis have close resemblance with the viral hepatitis-clinically, biochemically and histologically. Drugs also cause of chronic hepatic disease as chronic hepatitis, fatty liver, cirrhosis and several vascular lesions of the liver.

In many instances drug induced hepatitis proves indistinguishable from viral hepatitis. Chemically induced hepatic injury for experimental studies should be severe enough to cause cell death or to modify hepatic functions. The mechanism of acute hepatic injury depends upon the chemical compound and the species of animals used. Many chemicals produce parenchymal damage, arrest bile flow and cause jaundice (choleretic injury).

In the present invention the applicants have studied hepatoprotective activity against $CCl_4$, paracetamol (APAP, acetaminophen), D-galactosamine and alcohol induced hepatotoxicity.

OBJECTS OF THE INVENTION

The main object of the present invention is to provide a pharmaceutical composition comprising a bioactive compound trans-tetracos-15-enoic acid.

Another object of the present invention is to provide a process for the isolation of trans-tetracos-15-enoic acid from a plant source *Indigofera tinctoria* having significant dose-dependent hepatoprotective activity.

Another object of the present invention is to provide a well identified single constituent of plant origin for use in therapeutics.

Yet another object of the present invention provides a method of treatment of mammals and humans for hepatotoxicity.

SUMMARY OF THE INVENTION

The present invention relates to a pharmaceutical composition comprising a bioactive compound trans-tetracos-15-enoic acid and a process for the isolation of trans-tetracos-15-enoic acid from a plant source viz., *Indigofera tinctoria*. The present invention also provides a method for the treatment of acute hepatitis using this compound.

DETAILED DESCRIPTION OF THE INVENTION

Accordingly, the present invention provides a pharmaceutical composition comprising an effective amount of bioactive trans-tetracos-15-enoic acid extracted from a plant source *Indigofera tinctoria*, used to treat subjects with hepatic disorders.

An embodiment of the present invention, wherein said composition along with dehydrocholic acid is used for the enhancement of choleretic activity.

Another embodiment of the present invention wherein trans-tetracos-15-enoic acid is used singly or in combination with pharmaceutically acceptable additives.

Yet another embodiment of the present invention wherein the pharmaceutically acceptable additives are selected from the group consisting of carriers, diluents, solvents, filters lubricants, excipients, binder or stabilizers.

Still another embodiment of the present invention wherein the said composition is used for both preventive and curative properties.

Yet another embodiment of the present invention wherein said composition is used systemically, orally or by any clinically/medically accepted methods.

Still another embodiment of the present invention wherein the composition is used to treat hepatic disorders that are clinically, biochemically and histologically similar to that of viral hepatitis, chronic hepatitis, fatty liver, cirrhosis and several vascular lesions of the liver.

Yet another embodiment of the present invention wherein said composition is used to treat damage induced by hepatotoxins.

Still another embodiment of the present invention wherein the hepatotoxins are selected from the group comprising Galactosamine, Paracetamol, Carbon tetrachloride and alcohol.

Yet another embodiment of the present invention wherein the subjects is selected from the group consisting of mammals and humans, preferably humans.

Still another embodiment of the present invention wherein the dosage for treating $CCl_4$ induced hepatotoxicity in mammals is in the range of 10–100 mg/kg body weight.

Yet another embodiment of the present invention wherein the preferred dosage for treating $CCl_4$ induced hepatotoxicity in mammals is in the range of 50–100 mg/kg body weight.

Still another embodiment of the present invention wherein the hepatoprotective activity in $CCl_4$ induced hepatotoxic mammals is upto 88%.

Yet another embodiment of the present invention wherein the dosage for treating acetaminophen induced hepatotoxicity in mammals is in the range of 10–100 mg/kg body weight.

Still another embodiment of the present invention wherein the preferred dosage for treating acetaminophen induced hepatotoxicity in mammals is in the range of 50–100 mg/kg of body weight.

Yet another embodiment of the present invention wherein the hepatoprotective activity in acetaminophen induced hepatotoxicity in mammals is upto 86%.

Still another embodiment of the present invention wherein the dosage for treating Galactosamine induced hepatotoxicity in mammals is in the range of 10–50 mg/kg of body weight.

Yet another embodiment of the present invention wherein the preferred dosage for treating D-Galactosamine induced hepatotoxicity is in the range of 25–50 mg/kg of body weight.

Still another embodiment of the present invention wherein the hepatoprotective activity in Galactosamine induced hepatotoxicity in mammals is upto 73%.

Yet another embodiment of the present invention wherein the dosage for treating alcohol induced hepatotoxicity in mammals is in the range of 10–50 mg/kg of body weight.

Still another embodiment of the present invention wherein the preferred dosage for treating alcohol induced hepatotoxicity is in the range of 25–50 mg/kg of body weight.

Yet another embodiment of the present invention wherein the hepatoprotective activity in alcohol induced hepatotoxicity in mammals is upto 100%.

Still another embodiment of the present invention wherein the preferred dosage for treating hepatic disorders in mammals is 1 about 50–100 mg/kg of body weight.

Yet another embodiment of the present invention wherein the preferred dosage for treating hepatic disorders in human beings is about 10–15 mg/kg of body weight.

The invention also provides a process for the isolation of trans-tetracos-15-enoic acid, a bioactive constituent from plant *Indigofera tinctoria*, said process comprising the steps of:

(a) extracting the powdered plant parts with an aliphatic hydrocarbon solvent at a temperature in the range of 60–80° C. for about 20–30 hours;

(b) triturating the extract of step (a) with a ketonic solvent;

(c) separating the solvent soluble portion of step (b) and the residue by using silica gel bed;

(d) subjecting the residue of step (c) to column chromatography by eluting with a mixture of organic solvents of increasing polarity to yield a bioactive fraction; and (e) resolving fraction as obtained in step (d) by high performance liquid chromatography and crystallizing with an alcoholic solvent to obtain the bio-active constituent trans-tetracos-15-enoic acid.

Yet another embodiment of the present invention wherein alternatively, the fraction obtained in step (d) when subjected to semipreparative high performance liquid chromatography, yields bioactive constituent trans-tetracos-15-enoic acid.

Still another embodiment of the present invention wherein the plant parts used are aerial parts selected from the group consisting of leaves, stem and bark.

Yet another embodiment of the present invention wherein the hydrocarbon solvent is selected from the group consisting of petroleum ethane, n-hexane, cyclohexane or ligroin and preferably petroleum ether.

Still another embodiment of the present invention wherein in the ketonic solvent is selected from the group consisting of acetone, ethyl-methyl-ketone, or methyl isobutyl ketone.

Yet another embodiment of the present invention wherein the solvents used for eluting the column to obtain hepatoprotective fraction are selected from the group consisting of petroleum ether, n-hexane, chloroform, ethyl acetate, a mixture thereof and preferably a mixture of petroleum ether and ethyl acetate.

Still another embodiment of the present invention wherein in step (d), the solvent used for performing HPLC is a mixture of Acetonitrile and $H_2O$ in the ratio of 95:5.

Yet another embodiment of the present invention wherein in step (e) the HPLC purified compound is further purified by crystallizing with an alcoholic solvent selected from methanol and isopropanol.

Still another embodiment of the present invention wherein the hepatoprotective fraction thus obtained is designated as Indigotone consisting of a mixture of three compounds.

Yet another embodiment of the present invention wherein the percentage of mixture of three compounds of hepatoprotective fraction is 11–12%, 12–13% and 75–77% respectively.

The present invention further provides a method of treating subjects with liver disorders, the said method comprising administering a pharmaceutically effective dosage of trans-tetracos-15-enoic acid.

Yet another embodiment of the present invention, a method wherein trans-tetracos-15-enoic acid is used to treat liver disorders caused by Galactosamine, Paracetamol, Carbon tetrachloride and alcohol.

Still another embodiment of the present invention, a method wherein the dosage for $CCl_4$ induced hepatotoxicity in mammals is in the range of 10–100 mg/kg body weight.

Yet another embodiment of the present invention, a method wherein the preferred dosage for $CCl_4$ induced hepatotoxicity in mammals is in the range of 50–100 mg/kg body weight.

Still another embodiment of the present invention, a method wherein the hepatoprotective activity in $CCl_4$ induced hepatotoxic mammals is upto 88%.

Yet another embodiment of the present invention, a method wherein the dosage for acetaminophen induced hepatotoxicity in mammals is in the range of 10–100 mg/kg body weight.

Still another embodiment of the present invention, a method wherein the preferred dosage for acetaminophen induced hepatotoxicity in mammals is in the range of 50–100 mg/kg of body weight.

Yet another embodiment of the present invention, a method wherein the hepatoprotective activity in acetaminophen induced hepatotoxicity in mammals is upto 86%.

Still another embodiment of the present invention, a method wherein the dosage for Galactosamine induced hepatotoxicity in mammals is in the range of 10–50 mg/kg of body weight.

Yet another embodiment of the present invention, a method wherein the preferred dosage for D-Galactosamine induced hepatotoxicity is in the range of 25–50 mg/kg of body weight.

Still another embodiment of the present invention, a method wherein the hepatoprotective activity in Galactosamine induced hepatotoxicity in mammals is upto 73%.

Yet another embodiment of the present invention, a method wherein the dosage for alcohol induced hepatotoxicity in mammals is in the range of 10–50 mg/kg of body weight.

Still another embodiment of the present invention, a method wherein the preferred dosage for alcohol induced hepatotoxicity is in the range of 25–50 mg/kg of body weight.

Yet another embodiment of the present invention, a method wherein the hepatoprotective activity in alcohol induced hepatotoxicity in mammals is upto 100%.

Still another embodiment of the present invention, wherein the dosage for the enhancement of cholretic activity is in the range of 20–50 mg/kg of body weight.

Yet another embodiment of the present invention, the enhanced cholretic activity in mammals is upto 43%.

Still another embodiment of the present invention, a method wherein trans-tetracos-15-enoic acid is used singly or in combination with pharmaceutically acceptable carriers.

Yet another embodiment of the present invention, a method wherein the trans-tetracos-15-enoic acid is administered to a subject in combination with pharmaceutically acceptable additives, carriers, diluents, solvents, filters, lubricants, excipients, binder or stabilizers.

Still another embodiment of the present invention, a method wherein the desired dosage is administered for both preventive and curative properties.

Yet another embodiment of the present invention, a method wherein trans-tetracos-15-enoic acid is administered systemically, orally or by any clinically/medically accepted methods.

Still another embodiment of the present invention, a method wherein the subject is selected from animals, mammals, and preferably humans.

Still yet another embodiment of the present invention, a method wherein the preferred dosage for hepatic disorders in mammals is 1 about 50–100 mg/kg of body weight.

Yet another embodiment of the present invention, a method wherein the preferred dosage for human beings is about 10–15 mg/kg of body weight.

The invention is further explained in the form of following preferred embodiments.

Chromatographic fractionation of *Indigofera tinctoria* extract by a host of procedures viz., CC, MPLC & Centrifugal partition chromatography yielded four fractions designated as A, B, C & D respectively.

Pharmacological evaluation of these fractions showed that the hepatoprotective activity has got concentrated in fraction D, which exhibited dose-dependant response from 6.25 mg-Kg −1 P.O. in experimental animals. HPLC NP-SiO2, 10 mµ $CH_3OH:CHCl_3$ 10:90, or RP-C18, $CH_3CN:H_2O$ 95:5, isocratic elution, $\lambda=254$ nm) indicated fraction D to be composed of three constituents, compound A-11–12%, Compound B=12–13% and compound C=75–77%.

The fraction, which is designated as 'Indigotone' on CC and semi preparative HPLC yielded pure compound C. The compound on pharmacological evaluation showed dose dependent hepatoprotective activity in experimental animals from 12.5 mg-Kg−1 onwards.

Compound (C) is determined to be trans-tetracos-15-enoic acid on the bases of spectral data, viz., IR, UV, NMR (1H & 13C) & MS data.

This constitutes first observation and isolation of trans-tetracos-15-enoic acid from *Indigofera tinctoria*.

The hepatoprotective constituent obtained by the process of the present invention is present to the extent of 0.09–0.11% on the basis of dried plant material.

The invention is described with reference to the examples given below which should not, however, be construed to limit the scope of present invention.

Treatment with Bio-Active Compound of the Present Invention and Silymarin (Conventional Drug):

Freshly prepared suspension (1%, w/v) in 0.2% gum acacia in normal saline is used for all the experiments except for toxicity studies where (10%, w/v) suspension is used. Silymarin suspension (1%, w/v) in 0.2% gum acacia is used as a reference standard (positive control).

EXAMPLE 1

Dried aerial portion of the plant (1.3 Kg) is powdered, Soxhletted with petroleum ether (60–80° C.) for 30 hours. The resultant extract is concentrated and dried. DarkGreen semisolid residue (31 g), is triturated with acetone (5×200 ml) and acetone soluble portion is concentrated under reduced pressure to get a residue (21 g). The residue is adsorbed on $SiO_2$ gel (63 g, 100–200 mesh) and charged on a glass column (diameter 5-cm, height 85 cm), packed with SiO2 gel (250 g, 100–200 mesh). The column is eluted with petroleum ether: ethyl acetate mixtures of increasing polarity and finally with ethyl acetate.

The fractions eluted with petroleum ether: ethyl acetates (95:5) are pooled and the residue is designated as 'Indigotone', a mixture of three compounds (A-12%, B-14%, and C-74%). The fraction is subjected to HPLC (RP-18, 10 mµ, $CH_3CN:H_2O$, 95:5, $\lambda$max 254) to yield 1.1 g of pure C. Further purification is attained by crystallization from methanol (−20° C.). Purified constituent (m.p. 61° C.) is determined to be trans-tetracos-15-enoic acid on the base of co-TLC and spectral data.

EXAMPLE 2

Dried and powdered aerial portion of the plant material (650 g) is extracted with boiling hexane (2.5 L) for 20 hours. The resulting extract is subjected to desolventation under reduced pressure yielding a dark green viscous residue (16 g). The residue is triturated with ethyl methyl ketone (4×250 ml) and extracted material is concentrated and dried to get (11 g) of a semisolid material. The material is observed to be a complex mixture on TLC plate and thus is subjected to CC on $SiO_2$ gel. The column is eluted with (a) dichloromethane (1.5 L), (b) dichloromethane-ethyl acetate (98:2,2 L), (c) dichloromethane-ethyl acetate (95:5, 2 L), (d) dichloromethane-ethyl acetate (1 L). Solid residue (1 g) obtained from fraction (d) is designated as 'Indigotone'. HPLC output indicated Indigotone to be composed of three constituents viz., the most polar compound (A) 12%, constituent of medium polarity (B) 13% and the least polar compound (C) 75%.

Semipreparative HPLC (RP-C18, 10 mµ, $CH_3CN:H_2O$ 95:5, $\lambda$max 254 nm) with isocratic elution yielded pure C (600 mg). It is further purified by crystallization from isopropanol (−20° C.). Purified constituents, m.p. (61° C.) is identified to be trans-tetracos-15-enoic acid on the basis of spectral data, trans-tetracos-15-enoic acid has been evaluated for its hepatoprotective activity against $CCl_4$ hepatotoxin using commercially available Silymarin as reference materials. The comparative data have been provided in the TABLE-1.

To assess the efficacy of the drug, pharmacological studies are conducted on Wistar albino rats (150–180 g) and Swiss albino mice (25–30 g) of either sex, colony—bred in-house. After procurement, all the animals are divided into different groups and are left for one week for acclimatization in an experimentation room and are maintained on standard conditions (23±2° C., 60–70% relative humidity and 12 hours photo period). The animals are fed with standard rodents' pellet diet and water ad libitum. There are six animals in each group except for general behavior and acute toxicity studies where ten animals are used in each group.

The following hepatotoxins are used in the present invention to assess the efficacy of the drug:

(a) Carbon tetrachloride ($CCl_4$): One of the most powerful hepatotoxins (in terms of severity of injury) Carbon tetrachloride ($CCl_4$) as it causes toxic necrosis which leads to biochemical changes having clinical features similar to those of acute viral hepatitis (Vogel, 1977, Bramanti et. al., 1978, Kumar et. al., 1992). Liver injury is produced by administration of $CCl_4$ mixed with liquid paraffin. Animals are given single dose of $CCl_4$ (50 $\mu l.kg^{-1}$, p.o.) in acute single treatment and (0.5 $ml.kg^{-1}$, p.o.) in case of multi-treatment with drug. It is administered orally (p.o) by gastric intubation. The control animals received the equal volume of liquid paraffin. The results have been recorded in TABLES 1–5

(b) Paracetamol (APAP, acetaminophen): It is a therapeutic agent widely used as analgesic/antipyretic drug. When taken in large doses it causes hepatic necrosis which leads to biochemical changes having clinical features similar to those of acute viral hepatitis in humans (Proudfoot and Wright, 1970). The similar effect is observed in animals. The toxic effect can be potentiated if it is given several hours after the anesthetic ether inhalation (Wells et. al., 1985). Liver injury is induced by injecting paracetamol (200 $mg.kg^{-1}$) interaperitoneally in normal saline (pH 9.4) six hour after inhalation of anesthetic ether (4 ml/4 min/6 animals) in a closed chamber. The control animals received the equal volume of vehicle. The results have been recorded in TABLES 6–7.

(c) D-Galactosamine: It is one of the toxins that induce hepatic inflammatory conditions in the rat liver that clinically resembles to viral hepatitis. The mechanism of GalN induced liver injury has been extensively examined and this model is now accepted as one of the authentic systems of liver damage (Bauer et. al., 1974, Al-Tuwaijiri et. al., 1981).

The data have been recorded in TABLES 8–9.

Hepatic damage is produced by injecting GalN (300 $mg.kg^{-1}$) subcutaneously in normal saline. The control animals received the equal volume of vehicle.

EXAMPLE 3

Hexobarbitone Induced Narcosis:

The different doses of TCA, silymarin and vehicle (normal saline) are fed to different groups of mice only once at 1 hour before hepatotoxin ($CCl_4$, 50 $\mu l.kg^{-1}$, p.o.) administration. Animals are given Hexobarbitone (60 $mg.kg^{-1}$, i.p.) 2 hours after hepatotoxin and "sleep time" (Fujimoto, 1960; Dreyfuss, 1970) of all the animals is monitored. The time of onset of loss of righting reflex to the recovery in minutes is taken as the duration of sleep. (Table 1).

EXAMPLE 4

Zoxazolamine-Induced Paralysis:

The different doses of TCA, silymarin and vehicle (normal saline) are fed to different groups of mice only once 1 hour before hepatotoxin ($CCl_4$, 50 $\mu l.kg^{-1}$, p.o.) administration. Animals are given Zoxazolamine (70 $mg.kg^{-1}$, i.p.) 2 hours after hepatotoxin and "paralysis time" (Conney, 1960) of all the animals is monitored. The time of onset of paralysis to the recovery in minutes is taken as the duration of paralysis. (Table 1).

EXAMPLE 5

Effect on Serum and Hepatic Biochemical Parameters:

I) $CCl_4$ induced hepatotoxicity:

(a) Treatment of test material before and after hepatotoxin:

The different doses of, silymarin and vehicle (normal saline) are fed to different groups of rats at 48, 24, 2 hours before and 6 hours after hepatotoxin ($CCl_4$, 0.5 $ml.kg^{-1}$, p.o.) intoxication. Blood is collected from orbital sinus in all the animals 18 hours after last treatment and serum separated for different estimations. All the animals are then killed by decapitation, their livers are quickly excised, cleaned of adhering tissue, weighed and homogenized in phosphate buffer saline for the analysis of hepatic parameters (Agarwal and Mehendale, 1983, Klingensmith and Mehendale, 1982, Zimmerman, 1973, Edmondson and Peter, 1985, Mitchell, et al, 1973). (Tables 2–4).

(b) Treatment of Test Material After Hepatotoxin (Curative Study, Post Treatment)

The different doses of TCA, silymarin and vehicle (normal saline) are fed to different groups of rats at 6, 24 and 48 hours, after hepatotoxin ($CCl_4$, 0.5 $ml.kg^{-1}$, p.o.) intoxication. Blood is collected from the orbital sinus in all the animals 2 hours after last treatment and serum separated for different estimations. A portion of the liver is processed for histopathological studies. (Table 5).

II) Paracetamol Induced Hepatotoxicity:

(a) Treatment of Test Material Before and After Hepatotoxin:

The different doses of TCA, silymarin and vehicle (normal saline) are fed to different groups of mice at 72, 48, 24 hours, 1 hour before diethyl-ether inhalation and 1 hour after hepatotoxin (paracetamol, 200 $mg.kg^{-1}$, i.p.) given 6 h after exposure to diethyl-ether. Blood is collected from orbital sinus in all the animals 18 hours after last treatment and serum separated for different estimations. A portion of the liver is processed for histopathological studies. (Table 6)

(b) Treatment of Test Material After Hepatotoxin (Curative Study, Post Treatment)

The different doses of TCA, silymarin and vehicle (normal saline) are fed to different groups of mice at 1, 24, 48 hours, and 72 hours after hepatotoxin (paracetamol, 200 $mg.kg^{-1}$, i.p.). intoxication. Blood is collected from the orbital sinus in all the animals 2 hours after last treatment and serum separated for different estimations. All the animals are then killed by decapitation, their livers are quickly excised, cleaned of adhering tissue, weighed and homogenised in phosphate buffer saline for the analysis of hepatic parameters. A portion of the liver is processed for histopathological studies. (TABLE 7)

III) D-Galactosamine Induced Hepatotoxicity:

(a) Treatment of Test Material Before and After Hepatotoxin:

The different doses of TCA, silymarin and vehicle (normal saline) are fed to different groups of mice at 48, 24, 2 hours before and 6 hours after hepatotoxin (GalN, 300 mg.kg$^{-1}$, s.c.) intoxication. Blood is collected from orbital sinus in all the animals 18 hours after last treatment and serum separated for different estimations. All the animals are then killed by decapitation, their livers are quickly excised, cleaned of adhering tissue, weighed and homogenised in phosphate buffer saline for the analysis of hepatic parameters. A portion of the liver is processed for histopathological studies. (Table 8)

(b) Treatment of Test Material After Hepatotoxin (Curative Study, Post Treatment)

The different doses of, silymarin and vehicle (normal saline) are fed to different groups of rats at 6, 24, and 48 hours, after hepatotoxin (GalN, 300 mg.kg$^{-1}$, s.c.) intoxication. Blood is collected from the orbital sinus in all the animals 2 h after last treatment and serum separated for different estimations. All the animals are then killed by decapitation, their livers are quickly excised, cleaned of adhering tissue, weighed and homogenised in phosphate buffer saline for the analysis of hepatic parameters. A portion of the liver is processed for histopathological studies. (Table 9)

IV) Alcohol Induced Hepatotoxicity:

Liver lesions are induced by daily feeding of alcohol 376 mg.kg$^{-1}$ (p.o.) for six weeks to the different groups of rats. In the last two weeks of feeding of alcohol, different doses of TCA or silymarin are also fed daily 30 minutes after alcohol to the respective groups. Blood is collected from the orbital sinus in all the animals 2 h after the last treatment administered and serum separated for different estimations. All the animals are then killed by decapitation, their livers are quickly excised, cleaned of adhering tissue, weighed and homogenised in phosphate buffer saline for the analysis of hepatic parameters. (Tables 10&11)

Parameters Studied:

GPT and GOT: Pyruvate formed by transamination reaction is determined spectrophotometerically after reaction with 2,4-dinitrophenylhydrazine (Reitman and Frankel, 1957).

ALP: p-nitrophenol formed in alkaline medium is measured spectrophotometerically using p-nitrophenyl phosphate as substrate (Waler and Schutt, 1974).

Bilirubin: Total bilirubin is measured by diazotization reaction with NaNO$_2$ (Malloy and Evelyn, 1937)

Triglycerides: Triglycerides from serum are extracted with isopropanol and sopanified with KOH. The liberated glycerol is converted to formaldehyde by periodate and determined after reaction with acetyl acetone. Triolein is used as standard (Neri and Firings, 1973).

Glutathione: It is determined after de-proteination by reaction with DTNB (Ellman 1959 as modified by David 1987).

Lipid peroxidation: Thiobarbituric acid reacting substances are determined spectrophotometerically at 535 nm.

Drug metabolising enzymes: N-demethylase and Aniline hydroxylase are determined by spectrophotometeric methods however NADPH is used instead of NADPH generating system. (Imai Y, et al, 1966)

G-6-pase: Inorganic phosphate liberated from glucose-6-phosphate is measured with Amminonapthol sulphonic acid after reaction with ammonium molybdate. (Huijing, F., 1974) Glycogen and enzymes of glycogen metabolism. In: Clinical Biochemistry, Principles and Methods., H. Ch. Curtius and M. Roth (Eds.) Vol. 2., Walter de. Gruyter, Berlin., N.Y. Pp. 1208–1235.

SDH: Succinate dehydrogenase activity is measured using potassium ferricyanide in phosphate buffered medium. Slater and Bonner. (1952). Effect of fluoride on the Succinate oxidase system. Biochemical Journal 52, 185–196.

Protein: The protein is precipitated with TCA and dissolved in alkaline medium. The protein is measured by Folin's reagent. Lowery, O. H., Rosebrough, N. J., Farr, A. L. and Randle, R. J. (1951). Protein measurement with the Folin phenol Reagent. J. Biol. Chem. 193, 265–275.

GGT: p-nitroaniline formed γ-glutamyl p-nitroanilide in glycylglycine buffer measured at 405. nm. Szasz, g. (1976). Clin. Chem. 22, 2051–2055.

Hepatoprotective Activity:

Hepatoprotective activity (H) is calculated by the following equation:

$$H = [1 - (TC - V/VC - V)] \times 100$$

Where TC, VC, and V are drug+toxin, vehicle+toxin and vehicle treated groups of animals respectively.

EXAMPLE 6

Effect on Bile Flow and Bile Solids

The liver, by producing bile, plays an important role in digestion. The presence of bile in the intestine is necessary to accomplish the digestion and absorption of fats as well as absorption of the fat-soluble vitamins—A, D, E & K. Bile is also an important vehicle of excretion. It removes many drugs, toxins, bile pigments and various inorganic substances either derived from the diet or synthesized by the body as cholesterol or as cholic acid. Increase in the bile flow is suggestive of stimulating action of liver microsomal enzymes. Effect on the liver bile flow of test drug and that of vehicle is carried out after cannulating the bile duct in normal anaesthesied rats. Bile collected is from each animal from 0–5 hours (Klaassen, 1969, Donal et al. 1953). (TABLE 12)

Histopathological Studies:

A portion of the liver after treatment of hepatotoxin (GalN, CCl$_4$, and paracetamol) and test material is processed for histopathological studies by routine hematoxyline and eosin stained sections (Krajian, A. A., 1963).

General Behavior and Acute Toxicity:

Using different doses (10, 30, 100, 1200, 1400, 1600, 1800 and 2000 mg.kg$^{-1}$) of TCA given orally to the groups of 10 mice for each dose, while one group with same number of mice served as control. The animals are observed continuously for 1 hour and then half hourly for 4 hours for any gross behavioral changes and general motor activity, writhing, convulsion, response to tail pinching, gnawing, piloerection, pupil size, fecal output, feeding behaviour etc. and further up to 72 hours for any mortality. Acute LD$_{50}$ values in mice are calculated by the method of Miller and Tainter, (1944). Mortality of animals in all the groups used in different models for determining hepatoprotective activity during the period of treatment is also recorded as a rough index of subacute toxicity.

Statistical analysis: The data obtained are subjected to statistical analysis using ANOVA for comparing different groups (Armitage, 1987) and Dunnett's t test for control and test groups (Dunnett, 1964). The regression coefficient (Slope b) correlation coefficient (r) with its p value and $ED_{50}$ with 95% confidence limit (CL) are determined by regression analysis using log dose and percent effect of adaptogenic activity (Swinscow, 1980). The two tailed paired student t test for comparing means before and after treatment and one tailed unpaired student t test for comparing control and drug treated groups (Ghosh, 1984) are used. The p value of less than 0.05 or less is taken as the criterion of significance.

These results clearly show that TCA obtained from the plant *Indigofera tinctoria* when given orally exhibited dose dependent hepatoprotective activity in pre-and post-treatment against $CCl_4$, paracetamol and galactosamine induced acute hepatic injury.

Human Dose:

Doses for human being can be calculated by equivalent surface area doses conversion factor (equivalency on the basis of mg/sqm).

Advantages of the Present Invention

1. Commercially available herbal hepatoprotective are not standardized chemically as well as biologically. Since the bioactivity of herbal preparations is mainly ascribed to secondary metabolites, efficacy is not achieved unless such preparations are standardized on the basis of a few chemical constituents.
2. Latest hepatoprotective drug marketed by Ranbaxy (India) Ltd. viz., Silymarin is a mixture of three constituents, whose relative proportions also varies from batch to batch.
3. Present invention provides a single bioactive constituent from *Indigofera tinctoria* having dose dependent activity in experimental animals against $CCl_4$, paracetamol and galactosamine as hepatotoxins.

TABLE 4

Hepatoprotective activity (in vivo) of synthetic TCA vis-a-vis natural fed at 48 h, 24 h, 2 h before and 6 h after $CCl_4$ (0.5 ml. $kg^{-1}$, p.o.) induced hepatic injury in rats[a].

| PARAMETERS | NATURAL TCA 50 mg. $kg^{-1}$, p.o. | SYNTHETIC TCA 50 mg. $kg^{-1}$, p.o. | SILYMARIN 50 mg. $kg^{-1}$, p.o. |
|---|---|---|---|
| | Percent Hepatoprotection | | |
| S GPT | 67.22 | 74.63 | 59.73 |
| S GOT | 59.38 | 62.16 | 53.89 |
| S ALP | 72.15 | 81.78 | 67.87 |
| S BILIRUBIN | 62.22 | 55.55 | 51.11 |
| S TRIGLYCERIDES | 63.77 | 66.05 | 41.91 |
| HEPATIC LP | 61.72 | 64.33 | 77.58 |
| HEPATIC GSH | 59.06 | 52.92 | 61.98 |

[a]Values represent the mean ± SE and within parentheses hepatoprotective activity percent mean ± SE of six animals in each group.

TABLE 3

Hepatoprotective activity (in vivo) of TCA (Synthetic) fed at 48 h, 24 h, 2 h before and 6 h after $CCl_4$(0.5 ml.$kg^{-1}$, p.o.) induced hepatic injury in rats[a].

| Treatment | Dose mg/kg p.o. | GPT (Units) | GOT (Units) | ALP[b] | Bilirubin (mg %) | Triglycerides (mg %) | Lipid peroxidation[c] | Glutathione[d] |
|---|---|---|---|---|---|---|---|---|
| | | Serum parameters | | | | | Hepatic parameters | |
| Vehicle Control | — | 108.44 ± 16.05 | 119.12 ± 14.92 | 32.51 ± 1.94 | 0.13 ± 0.02 | 11.66 ± 0.40 | 43.13 ± 3.16 | 5.21 ± 0.28 |
| Vehicle + $CCl_4$ | — | 1821.52 ± 126.46 | 1062.29 ± 58.28 | 88.23 ± 6.60 | 0.72 ± 0.03 | 46.08 ± 3.84 | 89.38 ± 7.51 | 2.86 ± 0.43 |
| TCA Alone | 100 | 87.25 ± 23.80 | 103.37 ± 18.66 | 27.25 ± 1.72 | 0.18 ± 0.02 | 9.02 ± 0.84 | 40.41 ± 2.84 | 6.02 ± 0.35 |
| TCA + $CCl_4$ | 12.5 | 113.95 ± 76.67** (39.84 ± 4.47) | 798.85 ± 45.04** (27.93 ± 4.77) | 67.10 ± 4.28** (38.01 ± 7.72) | 0.56 ± 0.02** (26.60) | 40.38 ± 2.86[NS] (23.14 ± 4.13) | 73.33 ± 6.64[NS] (34.70 ± 14.35) | 3.61 ± 0.37[NS] (38.79 ± 12.39) |
| TCA + $CCl_4$ | 25 | 973.56 ± 76.45** (49.49 ± 4.46) | 623.73 ± 57.95** (46.49 ± 6.14) | 61.53 ± 3.35** (47.92 ± 5.94) | 0.47 ± 0.02** (42.90 ± 3.83) | 34.48 ± 3.29* (33.70 ± 9.58) | 66.09 ± 3.56* (50.34 ± 7.71) | 3.87 ± 0.21[NS] (42.98 ± 8.70) |
| TCA + $CCl_4$ | 50 | 829.44 ± 87.07** (57.91 ± 5.08) | 565.31 ± 60.33** (52.69 ± 6.39) | 53.85 ± 3.49** (61.70 ± 6.22) | 0.43 ± 0.02** (49.15 ± 3.96) | 28.03 ± 2.87** (52.45 ± 8.35) | 59.60 ± 6.06** (64.39 ± 13.11) | 4.13 ± 0.41[NS] (58.44 ± 14.85) |
| TCA + $CCl_4$ | 100 | 690.23 ± 61.25** (66.04 ± 3.58) | 445.55 ± 39.39** (65.39 ± 4.18) | 48.96 ± 4.09** (70.47 ± 7.35) | 0.36 ± 0.02** (61.02 ± 4.13) | 22.77 ± 1.60** (67.71 ± 3.37) | 48.69 ± 4.37** (87.94 ± 9.44) | 4.50 ± 0.30** (69.92 ± 12.77) |

TABLE 3-continued

Hepatoprotective activity (in vivo) of TCA (Synthetic) fed at 48 h, 24 h, 2 h before and 6 h after CCl$_4$(0.5 ml.kg$^{-1}$, p.o.) induced hepatic injury in rats[a].

| Treatment | Dose mg/kg p.o. | Serum parameters | | | | | Hepatic parameters | |
|---|---|---|---|---|---|---|---|---|
| | | GPT (Units) | GOT (Units) | ALP[b] | Bilirubin (mg %) | Triglycerides (mg %) | Lipid peroxidation[c] | Glutathione[d] |
| Silymarin + CCl$_4$ | 50 | 840.86 ± 57.99** (57.25 ± 3.39) | 663.11 ± 49.03** (42.32 ± 5.19 | 56.00 ± 2.85** (57.84 ± 5.11) | 0.41 ± 0.02** 51.40 ± 4.77 | 32.26 ± 2.39** (40.15 ± 6.94) | 62.73 ± 5.39** (57.62 ± 11.66) | 4.46 ± 0.27* (68.01 ± 11.90) |

[a]Values represent the mean ± SE and within parentheses hepatoprotective activity percent mean ± SE of six animals in each group.
H: Hepatoprotective activity was calculated as {1 − (T − V/C − V)} × 100 where "T" is mean value of drug and CCl$_4$, "C" is mean value of CCl$_4$ alone and "V" is the mean value of vehicle treated animals.
Unit: each unit is μmole pyruvate/min/L.
[b]is μmole of p-nitrophenol formed/min/L,
[c]is n moles MDA/g liver.,
[d]is μmole GSH/g liver
p value
*< .05;
**< 0.01
NS> 0.05 (Dunnett's t - test).

TABLE 5

Hepatoprotective activity (in vivo) of TCA (Natural) fed at 6 h, 24 h, 48 h after CCl$_4$ (0.5 ml. kg$^{-1}$, p.o.) induced hepatic injury in rats[a].

| Treatment | Dose mg/kg p.o. | Serum parameters | | | | |
|---|---|---|---|---|---|---|
| | | GPT (Units) | GOT (Units) | ALP[b] | Bilirubin (mg %) | Triglycerides (mg %) |
| Vehicle Control | — | 91.50 ± 12.53 | 97.22 ± 7.75 | 23.50 ± 2.58 | 0.12 ± 0.02 | 8.11 ± 0.65 |
| Vehicle + CCl$_4$ | — | 1512.97 ± 72.25 | 776.34 ± 80.61 | 65.07 ± 6.11 | 0.88 ± 0.06 | 14.08 ± 1.00 |
| TCA Alone | 100 | 92.18 ± 15.75 | 82.13 ± 10.59 | 25.84 ± 2.32 | 0.16 ± 0.02 | 6.98 ± 0.86 |
| TCA + CCl$_4$ | 12.5 | 1001.86 ± 48.55** (35.59 ± 3.37) | 524.23 ± 34.93** (37.12 ± 5.14) | 51.81 ± 3.94$^{NS}$ (27.87 ± 9.48) | 0.54 ± 0.02** (44.52 ± 3.66) | 12.57 ± 0.61$^{NS}$ (24.12 ± 10.07) |
| TCA + CCl$_4$ | 25 | 772.68 ± 47.66** (51.52 ± 3.31) | 448.28 ± 54.88** (48.31 ± 8.808) | 50.92 ± 1.62* (34.03 ± 3.89) | 0.47 ± 0.03** (53.51 ± 4.06) | 11.81 ± 1.05$^{NS}$ (36.23 ± 18.23) |
| TCA + CCl$_4$ | 50 | 582.12 ± 37.7** (64.76 ± 2.62) | 365.43 ± 29.43** (60.50 ± 4.33) | 43.63 ± 2.82** (51.57 ± 6.78) | 0.39 ± 0.02** (64.25 ± 3.76) | 11.06 ± 0.61* (48.86 ± 10.64) |
| TCA + CCl$_4$ | 100 | 457.55 ± 18.18** (73.41 ± 1.26) | 318.96 ± 16.15** (67.35 ± 2.38) | 32.93 ± 2.13** (77.31 ± 5.13) | 0.29 ± 0.02** (76.54 ± 3.66) | 10.37 ± 0.65** (61.02 ± 11.24) |
| Silymarin + CCl$_4$ | 50 | 677.55 ± 53.72** (58.16 ± 3.74) | 413.03 ± 24.98** (53.49 ± 3.67) | 48.44 ± 2.98** (39.99 ± 7.17) | 0.46 ± 0.03** (55.26 ± 4.05) | 11.04 ± 0.54$^{NS}$ (42.48 ± 8.75) |

[a]Values represent the mean ± SE and within parentheses hepatoprotective activity percent mean ± SE of eight animals in each group.
H: Hepatoprotective activity was calculated as {1 − (T − V/C − V)} × 100 where "T" is mean value of drug and CCl$_4$, "C" is mean value of CCl$_4$ alone and "V" is the mean value of vehicle treated animals.
Unit: each unit is μmole pyruvate/min/L.
[b]is μmole of p-nitrophenol formed/min/L,
p value
*< .05;
**< 0.01
NS> 0.05 (Dunnett's t - test).

TABLE 6

Hepatoprotective activity (in vivo) of TCA (Natural) fed at 72 h, 48 h, 24 h, 1 h before inhalation of diethyl-ether and 1 h after acetaminophen (200. mg.kg$^{-1}$, i. p., 6 h after exposure to diethyl-ether) in mice[a].

| Treatment | Dose mg/kg, p.o. | Serum parameters | | | |
|---|---|---|---|---|---|
| | | GPT (Units) | GOT (Units) | ALP[b] | Triglycerides (mg %) |
| Vehicle Control | — | 179.47 ± 30.85 | 129.74 ± 27.28 | 25.06 ± 2.65 | 8.76 ± 0.93 |
| Vehicle + APAP | — | 2775.87 ± 138.60 | 1407.19 ± 51.34 | 57.21 ± 2.24 | 17.07 ± 1.33 |
| TCA Alone | 100 | 146.00 ± 32.15 | 106.86 ± 30.15 | 27.15 ± 2.92 | 7.77 ± 0.56 |
| TCA + APAP | 12.5 | 2182.19 ± 137.86 | 1079.43 ± 98.66 | 50.41 ± 3.07 | 14.72 ± 0.68 |
| | | (22.86 ± 5.31) | (25.66 ± 7.72) | (21.27 ± 9.50) | (28.28 ± 8.27) |
| TCA + APAP | 25 | 1696.53 ± 48.31 | 880.10 ± 60.29 | 46.23 ± 1.73 | 13.47 ± 0.89 |
| | | (41.57 ± 1.86) | (41.26 ± 4.72) | (34.15 ± 5.39) | (43.32 ± 10.80) |
| TCA + APAP | 50 | 1066.99 ± 118.14 | 619.36 ± 88.89 | 41.44 ± 1.27 | 12.34 ± 0.85 |
| | | (65.82 ± 4.55) | (61.67 ± 6.96) | (49.04 ± 3.94) | (56.84 ± 10.23) |
| TCA + APAP | 100 | 539.60 ± 51.65 | 310.53 ± 45.32 | 35.08 ± 2.18 | 10.87 ± 0.69 |
| | | (86.13 ± 1.99) | (85.85 ± 4.25) | (68.82 ± 6.78) | (74.48 ± 8.37) |
| Silymarin + APAP | 50 | 1060.09 ± 88.87 | 716.83 ± 44.44 | 42.53 ± 1.90 | 12.48 ± 0.86 |
| | | (65.97 ± 3.44) | (53.52 ± 2.17) | (45.66 ± 5.93) | (55.27 ± 10.39) |

[a]Values represent the mean ± SE and within parentheses hepatoprotective activity percent mean ± SE of eight animals in each group.
H: Hepatoprotective activity was calculated as $\{1 - (T - V/C - V)\} \times 100$ where "T" is mean value of drug and "APAP" C" is mean value of APAP alone and "V" is the mean value of vehicle treated animals.
Unit: each unit is μmole pyruvate/min/L.
[b]is μmole of p-nitrophenol formed/min/L,
p value
* < .0.05;
** < 0.01
NS > 0.05 (Dunnett's t - test).

TABLE 2

Hepatoprotective activity (in vivo) of TCA (Natural) fed at 48 h, 24 h, 2 h before and 6 h after CCl$_4$ (0.5 ml. kg$^{-1}$, p.o.) induced hepatic injury in rats[a].

| Treatment | Dose mg/kg p.o. | Serum parameters | | | | |
|---|---|---|---|---|---|---|
| | | GPT (Units) | GOT (Units) | ALP[b] | Bilirubin (mg %) | Triglycerides (mg %) |
| Vehicle Control | — | 130.91 ± 17.33 | 138.12 ± 32.21 | 21.60 ± 2.16 | 0.13 ± 0.02 | 8.71 ± 1.06 |
| Vehicle + CCl$_4$ | — | 1604.01 ± 100.32 | 980.50 ± 37.95 | 53.13 ± 3.56 | 0.79 ± 0.03 | 15.23 ± 1.58 |
| TCA Alone | 100 | 102.66 ± 28.41 | 110.53 ± 25.55 | 23.15 ± 2.92 | 0.17 ± 0.02 | 6.98 ± 0.79 |
| TCA + CCl$_4$ | 12.5 | 992.34 ± 73.25** | 695.16 ± 67.28** | 45.25 ± 2.37$^{NS}$ | 0.47 ± 0.01** | 13.51 ± 0.51$^{NS}$ |
| | | (41.52 ± 4.97) | (33.87 ± 7.99) | (26.32 ± 6.55) | (47.98 ± 2.02) | (26.40 ± 7.84) |
| TCA + CCl$_4$ | 25 | 924.39 ± 39.82** | 674.44 ± 53.20** | 39.48 ± 2.46** | 0.42 ± 0.01** | 12.11 ± 070$^{NS}$ |
| | | (46.10 ± 2.70) | (36.33 ± 6.32) | (43.28 ± 7.81) | (55.33 ± 2.86) | (47.72 ± 11.33) |
| TCA + CCl$_4$ | 50 | 636.60 ± 44.49** | 543.99 ± 79.93** | 35.19 ± 2.90** | 0.34 ± 0.01** | 11.89 ± 0.75$^{NS}$ |
| | | (65.66 ± 3.02) | (51.82 ± 9.94) | (56.81 ± 9.15) | (67.67 ± 2.30) | (51.77 ± 11.46) |
| TCA + CCl$_4$ | 100 | 419.72 ± 17.60** | 432.08 ± 37.88** | 30.14 ± 2.54** | 0.26 ± 0.02** | 11.20 ± 0.68$^{NS}$ |
| | | (80.39 ± 1.19) | (65.10 ± 4.50) | (72.92 ± 8.07) | (79.04 ± 3.57) | (61.75 ± 1.44) |
| Silymarin + CCl$_4$ | 50 | 809.18 ± 45.35** | 543.60 ± 45.91** | 36.24 ± 1.77** | 0.40 ± 0.03** | 12.07 ± 0.97$^{NS}$ |
| | | (54.04 ± 2.99) | (50.68 ± 6.36) | (53.56 ± 5.63) | (59.09 ± 5.44) | (48.46 ± 14.96) |

[a]Values represent the mean ± SE and within parentheses hepatoprotective activity percent mean ± SE of six animals in each group.
H: Hepatoprotective activity was calculated as $\{1 - (T - V/C - V)\} \times 100$ where "T" is mean value of drug and CCl$_4$, "C" is mean value of CCl$_4$ alone and "V" is the mean value of vehicle treated animals.
Unit: each unit is μmole pyruvate/min/L.
[b]is μmole of p-nitrophenol formed/min/L,
p value
* < .0.05;
** < 0.01
NS > 0.05 (Dunnett's t - test).

TABLE 1

Hexobarbitone sleep time and zoxazolamine paralysis time (in vivo) of TCA (Natural) fed at 1 h before CCl$_4$ (50 μl. kg$^{-1}$, p.o.) administration in mice[a]

| Treatment | Dose mg kg$^{-1}$ p.o. | Hexobarbitone Sleeping time (min) | Hepatoprotection (%) | Zoxazolamine Paralysis time (min) | Hepatoprotection (%) |
|---|---|---|---|---|---|
| Vehicle Control | — | 23.33 ± 1.76 | — | 21.33 ± 1.36 | — |
| Vehicle + CCl$_4$ | — | 55.66 ± 1.87b | — | 50.83 ± 3.10b | — |
| TCA Alone | 100 | 21.85 ± 1.34 | — | 19.94 ± 1.49 | — |
| TCA + CCl$_4$ | 12.5 | 44.16 ± 1.87*c | 35.55 ± 5.78 | 39.00 ± 1.93*c | 40.10 ± 6.55 |
| TCA + CCl$_4$ | 25 | 37.83 ± 2.31c | 55.14 ± 7.16 | 35.66 ± 3.28c | 51.40 ± 11.12 |
| TCA + CCl$_4$ | 50 | 31.66 ± 2.31c | 74.21 ± 6.27 | 30.00 ± 2.26c | 70.61 ± 7.68 |
| TCA + CCl$_4$ | 100 | 28.16 ± 2.30c | 85.04 ± 7.12 | 26.00 ± 1.93c | 84.17 ± 6.55 |
| Silymarin + CCl$_4$ | 50 | 36.33 ± 2.46c | 59.78 ± 7.60 | 34.66 ± 1.68c | 54.79 ± 5.72 |

[a]Values represent the mean ± SE of six animals in each group.
H: Hepatoprotective activity was calculated as {1 − (T − V/C − V)} × 100 where "T" is mean value of drug and CCl$_4$, "C" is mean value of CCl$_4$ alone and "V" is the mean value of vehicle treated animals.
[b]Difference in relation to vehicle treated control group.
[c]Difference in relation to CCl$_4$ control group.
p value
* < .0.05;
** < 0.01 (Dunnett's t - test).

TABLE 7

Hepatoprotective activity (in vivo) of TCA (Natural) fed at 1 h, 24 h, 48 h, 72 h after acetaminophen (200. mg. kg$^{-1}$, i. p. 6 h after exposure to diethyl-ether) in mice[a].

| Treatment | Dose mg/kg, p.o. | GPT (Units) | GOT (Units) | ALP[b] | Triglycerides (mg %) |
|---|---|---|---|---|---|
| Vehicle Control | — | 145.94 ± 21.48 | 129.74 ± 27.28 | 25.06 ± 2.65 | 8.76 ± 0.93 |
| Vehicle + APAP | — | 682.11 ± 83.73 | 1407.19 ± 51.34 | 57.21 ± 2.24 | 17.07 ± 1.33 |
| TCA Alone | 100 | 129.65 ± 24.84 | 133.77 ± 20.84 | 22.57 ± 2.95 | 7.43 ± 0.89 |
| TCA + APAP | 12.5 | 431.85 ± 25.52** (49.67 ± 2.81) | 1079.43 ± 98.66[NS] (25.66 ± 7.72) | 50.41 ± 3.07[NS] (21.27 ± 9.50) | 14.72 ± 0.68[NS] (28.28 ± 8.27) |
| TCA + APAP | 25 | 320.07 ± 41.33** (67.52 ± 7.71) | 880.10 ± 60.29* (41.26 ± 4.72) | 46.23 ± 1.73* (34.15 ± 5.39) | 13.47 ± 0.89[NS] (43.32 ± 10.80) |
| TCA + APAP | 50 | 282.74 ± 32.96** (74.48 ± 6.154.55) | 619.36 ± 88.89** (61.67 ± 6.96) | 41.44 ± 1.27** (49.04 ± 3.94) | 12.34 ± 0.85** (56.84 ± 10.23) |
| TCA + APAP | 100 | 235.89 ± 22.77** (83.33 ± 1.99) | 310.53 ± 45.32** (85.85 ± 4.25) | 35.08 ± 2.18** (68.82 ± 6.78) | 10.87 ± 0.69** (74.48 ± 8.37) |
| Silymarin + APAP | 50 | 1060.09 ± 88.87** (65.97 ± 3.44) | 348.64 ± 344.76** (55.22 ± 8.39) | 42.53 ± 1.90* (45.66 ± 5.93) | 12.48 ± 0.86* (55.27 ± 10.39) |

[a]Values represent the mean ± SE and within parentheses hepatoprotective activity percent mean ± SE of eight animals in each group.
H: Hepatoprotective activity was calculated as {1 − (T − V/C − V)} × 100 where "T" is mean value of drug and "APAP" C" is mean value of APAP alone and "V" is the mean value of vehicle treated animals.
Unit: each unit is μmole pyruvate/min/L.
[b]is μmole of p-nitrophenol formed/min/L,
p value
* < .0.05;
** < 0.01
[NS] > 0.05 (Dunnett's t - test).

TABLE 9

Hepatoprotective activity (in vivo) of TCA (Natural) fed at 6 h, 24 h, 48 h and 72 h after GalN (300. mg. kg$^{-1}$, s.c.) induced hepatic injury in rats[a].

| Treatment | Dose mg kg$^{-1}$, p.o. | GPT (Units) | GOT (Units) | Bilirubin (mg %) | ALP[b] | Triglycerides (mg %) |
|---|---|---|---|---|---|---|
| Vehicle Control | — | 95.23 ± 7.82 | 87.37 ± 6.88 | 0.15 ± 0.02 | 26.99 ± 2.53 | 5.79 ± 0.93 |
| Vehicle + GalN | — | 905.48 ± 58.27 | 705.43 ± 49.39 | 0.92 ± 0.03 | 60.78 ± 3.72 | 14.81 ± 2.54 |

TABLE 9-continued

Hepatoprotective activity (in vivo) of TCA (Natural) fed at 6 h, 24 h, 48 h and 72 h after GalN (300. mg. kg$^{-1}$, s.c.) induced hepatic injury in rats[a].

| Treatment | Dose mg kg$^{-1}$, p.o. | GPT (Units) | GOT (Units) | Bilirubin (mg %) | ALP[b] | Triglycerides (mg %) |
|---|---|---|---|---|---|---|
| TCA Alone | 50 | 105.02 ± 18.74 | 91.07 ± 10.52 | 0.19 ± 0.02 | 24.45 ± 2.76 | 6.44 ± 0.38 |
| TCA + GalN | 12.5 | 578.14 ± 57.37** (40.40 ± 7.08) | 494.53 ± 41.13** (34.12 ± 6.65) | 0.56 ± 0.03** (46.75 ± 3.74) | 46.03 ± 2.35$^{NS}$ (43.65 ± 6.96) | 11.85 ± 0.75$^{NS}$ (32.78 ± 8.37) |
| TCA + GalN | 25 | 518.66 ± 42.64** (47.74 ± 5.26) | 449.93 ± 31.58** (41.37 ± 5.10) | 0.46 ± 0.03** (59.74 ± 4.04) | 38.87 ± 2.62** (64.83 ± 7.74) | 10.48 ± 0.91$^{NS}$ (46.11 ± 9.77) |
| TCA + GalN | 50 | 412.17 ± 31.17** (60.88 ± 3.85) | 391.66 ± 29.53** (50.76 ± 4.78) | 0.35 ± 0.02** (73.16 ± 2.95) | 36.94 ± 1.87** (71.88 ± 5.54) | 9.23 ± 059* (61.84 ± 6.59) |
| Silymarin + GalN | 50 | 475.43 ± 53.47** (53.07 ± 6.60) | 393.83 ± 26.41** (50.41 ± 4.27) | 0.45 ± 0.03** (60.17 ± 4.17) | 45.24 ± 3.01$^{NS}$ (45.99 ± 8.91) | 12.39 ± 1.58$^{NS}$ (26.75 ± 17.58) |

[a]Values represent the mean ± SE and within parentheses hepatoprotective activity percent mean ± SE of six animals in each group.
H: Hepatoprotective activity was calculated as $\{1 - (T - V/C - V)\} \times 100$ where "T" is mean value of drug and CCl$_4$, "C" is mean value of CCl$_4$ alone and "V" is the mean value of vehicle treated animals.
Unit: each unit is μmole pyruvate/min/L.
[b]is μmole of p-nitrophenol formed/min/L,
p value
*< .0.05;
**< 0.01
$^{NS}$> 0.05 (Dunnett's t - test).

TABLE 8

Hepatoprotective activity (in vivo) of TCA (Natural) fed at 72 h, 48 h, 24 h, 2 h before and 6 h after GalN 300. mg. kg$^{-1}$, s.c.) induced hepatic injury in rats[a].

| Treatment | Dose mg kg$^{-1}$, p.o. | GPT (Units) | GOT (Units) | Bilirubin (mg %) | ALP[b] | Triglycerides (mg %) |
|---|---|---|---|---|---|---|
| Vehicle Control | — | 97.98 ± 9.97 | 116.94 ± 20.76 | 0.17 ± 0.02 | 22.92 ± 1.89 | 7.48 ± 0.85 |
| Vehicle + GalN | — | 1161.74 ± 54.83 | 859.24 ± 60.38 | 0.82 ± 0.03 | 59.26 ± 2.63 | 37.84 ± 2.58 |
| TCA Alone | 50 | 95.22 ± 8.74 | 122.47 ± 11.84 | 0.20 ± 0.02 | 19.84 ± 1.58 | 8.79 ± 0.55 |
| TCA + GalN | 12.5 | 743.62 ± 66.83** (39.30 ± 6.25) | 613.20 ± 65.19** (34.60 ± 7.57) | 0.56 ± 0.03** (39.49 ± 4.59) | 47.07 ± 2.98** (30.88 ± 7.77) | 26.49 ± 1.88* (37.38 ± 6.18) |
| TCA + GalN | 25 | 635.11 ± 54.67** (49.35 ± 5.16) | 505.26 ± 29.63** (47.68 ± 3.99) | 0.44 ± 0.05** (58.00 ± 3.86) | 40.49 ± 2.29** (51.62 ± 6.31) | 23.58 ± 2.02** (46.97 ± 6.67) |
| TCA + GalN | 50 | 413.53 ± 23.94** (70.34 ± 2.25) | 406.05 ± 25.82** (61.05 ± 3.48) | 0.36 ± 0.02** (70.76 ± 2.78) | 34.94 ± 1.43** (66.91 ± 3.92) | 21.37 ± 1.51** (54.25 ± 4.97) |
| Silymarin + GalN | 50 | 587.98 ± 54.59** (53.94 ± 5.13) | 458.13 ± 40.69** (54.03 ± 5.48) | 0.44 ± 0.02** (58.71 ± 4.13) | 42.08 ± 2.56** (47.25 ± 7.05) | 28.85 ± 1.85* (29.61 ± 6.08) |

[a]Values represent the mean ± SE and within parentheses hepatoprotective activity percent mean ± SE of six animals in each group.
H: Hepatoprotective activity was calculated as $\{1 - (T - V/C - V)\} \times 100$ where "T" is mean value of drug and CCl$_4$, "C" is mean value of CCl$_4$ alone and "V" is the mean value of vehicle treated animals.
Unit: each unit is μmole pyruvate/min/L.
[b]is μmole of p-nitrophenol formed/min/L,
p value
*< .0.05;
**< 0.01
$^{NS}$> 0.05 (Dunnett's t - test).

TABLE 10

Hepatoprotective activity (in vivo) of TCA (Natural) against alcohol induced hepatic damage in rats[a].

| Serum Parameters | Units | Gr. I Vehicle Control | Gr. II Vehicle + Alcohol | Gr. III TCA (25 mgkg$^{-1}$) + Alcohol | Gr. IV TCA (50 mgkg$^{-1}$) + Alocohol | Gr. V Silymarin (50 mg kg$^{-1}$) + Alcohol |
|---|---|---|---|---|---|---|
| SGOT | U/l | 296.00 ± 9.79 | 357.00 ± 33.39 | 310.00 ± 30.36*[b] | 295.00 ± 34.39*[b] | 333.00 ± 29.71**[b] |
| % protection | | — | — | 77.29 | 101.09 | 39.43 |
| SGPT | U/l | 199.00 ± 16.34 | 281.00 ± 12.39 | 234.00 ± 8.80**[b] | 220.00 ± 11.30**[b] | 224.00 ± 11.76**[b] |
| % protection | | — | — | 57.33 | 73.86 | 49.03 |

TABLE 10-continued

Hepatoprotective activity (in vivo) of TCA (Natural) against alcohol induced hepatic damage in rats[a].

| Serum Parameters | Units | Gr. I Vehicle Control | Gr. II Vehicle + Alcohol | Gr. III TCA (25 mgkg$^{-1}$) + Alcohol | Gr. IV TCA (50 mgkg$^{-1}$) + Alocohol | Gr. V Silymarin (50 mg kg$^{-1}$) + Alcohol |
|---|---|---|---|---|---|---|
| GGT | IU/l | 1.42 ± 0.303 | 2.69 ± 0.701 | 1.90 ± 0.447 | 1.54 ± 0.128 | 1.43 ± 0.157 |
|  | % protection | — | — | 63.00 | 90.00 | 100.00 |
| ALP | U/l | 14.00 ± 1.23 | 24.00 ± 1.60 | 16.00 ± 2.04***[b] | 14.60 ± 2.82***[b] | 13.80 ± 2.016**[b] |
|  | % protection | — | — | 80.00 | 95.00 | 100.00 |
| Protein | g/dl | 11.70 ± 3.14 | 10.50 ± 2.10 | 16.90 ± 3.78 | 12.60 ± 3.09 | 10.80 ± 3.26 |
|  | % protection | — | − 10.30 | 44.40 | 7.70 | −7.70 |

[a]Values represent the mean ± SE of six animals in each group.
H: Hepatoprotective activity was calculated as {1 − (T − V/C − V)} × 100 where "T" is mean value of drug and Alcohol "C" is mean value of Alcohol alone and "V" is the mean value of vehicle treated animals.
p value
* < .0.05;
** < 0.01
*** < 0.001 (Students's t - test). and others are not significant.

TABLE 11

Hepatoprotecive activity (in vivo) of RLJ-NE-598 (025)(F)(A$_3$)(N) against alcohol induced hepatic damage in rats[a].

| Hepatic Parameters | Units | Gr I Vehicle Control | Gr. II Vehicle + alcohol | Gr. III (F)(A$_3$)(N) (25 mgkg$^{-1}$) + Alcohol | Gr. IV (F)(A$_3$)(N) (50 mgkg$^{-1}$) + Alcohol | Gr. V Silymarin (50 mg kg$^{-1}$) + Alcohol |
|---|---|---|---|---|---|---|
| SDH | Units/g | 9.13 ± 0.196 | 7.58 ± 0.338**[b] | 7.79 ± 0.272 | 8.24 ± 0.390 | 8.18 ± 0.113*[c] |
|  | % protection | — | — | 14 | 43 | 39 |
| G-6-Pase | Units/g | 2.36 ± 0.235 | 1.73 ± 0.135 | 2.19 ± 0.465 | 2.20 ± 0.223 | 2.20 ± 0.356 |
|  | % protection | — | — | 73 | 75 | 75 |
| Protein | mg/g | 179.00 ± 8.23 | 168 ± 7.51 | 172 ± 20.430 | 174 ± 2.11 | 181 ± 6.89 |
|  | % Change | — | −7.1 | −3.9 | −2.8 | 1.1 |
| TG | mg/g | 15.22 ± 4.874 | 16.56 ± 1.496 | 14.75 ± 0.60 | 15.44 ± 1.073 | 14.67 ± 2.589 |
|  | % Change | — | 8.8 | −3.1 | 1.4 | −3.6 |

[a]Values represent the mean ± SE of six animals in each group.
H: Hepatoprotective activity was calculated as {1 − (T − V/C − V)} × 100 where "T" is mean value of drug and Alcohol "C" is mean value of Alcohol alone and "V" is the mean value of vehicle treated animals.
p value
* < .0.05;
** < 0.01 (Student's t - test). and others are not significant.

TABLE 12

Cholretic activity of TCA and dehydrocholic acid in rats[a].

| | | | Bile parameters[a] | |
|---|---|---|---|---|
| | | | % Increase (as compared to normal) | |
| Treatment | Dose mg. kg$^{-1}$ | Route | Bile flow (mg %) | Bile solids (mg %) |
| TCA | 50 | i.d. | 8.23 ± 1.71 | 13.40 ± 1.53 |
| TCA | 20 | i.v. | 43.63 ± 3.13 | 31.36 ± 4.09 |
| TCA | 50 | i.d. | 38.4 ± 2.76 | 28.13 ± 3.89 |

[a]Values represent mean ± SE of six animals in each group.
[b]Values represent mean ± SE of eight animals in each group.

The invention claimed is:

1. A pharmaceutical composition comprising an effective amount of an isolated and purified bioactive trans-tetracos-15-enoic acid extracted from an aerial part of *Indigofera tinctoria*, used for the treatment of subjects with hepatic disorders.

2. A composition according to claim 1 wherein trans-tetracos-15-enoic acid is used singly or in combination with pharmaceutically acceptable additives.

3. A composition according to claim 1 wherein the pharmaceutically acceptable additives are selected from the group consisting of carriers, diluents, solvents, filters lubricants, excipients, binder or stabilizers.

4. A composition according to claim 1 wherein said composition is used systemically, orally or by any clinically/medically accepted methods.

5. A composition according to claim 1, wherein the subjects is selected from the group consisting of humans and mammals, preferably humans.

6. A composition according to claim 1 in which said bioactive trans-tetracos-15-enoic acid is extracted by a process comprising extracting the powdered plant parts of a plant from the species *Indigofera tinctoria* with an aliphatic hydrocarbon solvent, obtaining a residue from the extract, purifying the residue by chromatography to yield a bioactive fraction and crystallizing bio-active trans-tetracos-15-enoic acid from the fraction using an alcoholic solvent.

7. The composition of claim 6 in which the extraction is performed at a temperature in the range of 60–80° C. for about 20–30 hours.

8. The composition of claim 6 in which the residue is obtained by triturating the extract with a ketonic solvent.

9. The composition of claim 6 in which the chromatography comprises claim 6 in which said process further comprises the use of one or more of: a) a silica gel bed; b) column chromatography by eluting with a mixture of organic solvents of increasing polarity to yield a bioactive fraction; and c) high performance liquid chromatography.

10. The composition of claim 6 in which the aliphatic hydrocarbon solvent is petroleum ether.

11. The composition of claim 6 in which the alcoholic solvent is methanol or isopropanol.

* * * * *

UNITED STATES PATENT AND TRADEMARK OFFICE
CERTIFICATE OF CORRECTION

PATENT NO. : 7,118,766 B2 Page 1 of 1
APPLICATION NO. : 10/073548
DATED : October 10, 2006
INVENTOR(S) : Sukhdev Swami Handa et al.

It is certified that error appears in the above-identified patent and that said Letters Patent is hereby corrected as shown below:

Column 23, line 7, "claim 6" should be -- claim 7 --.

Signed and Sealed this

Eighteenth Day of December, 2007

JON W. DUDAS
*Director of the United States Patent and Trademark Office*